US005425700A

United States Patent [19]
Aaserude et al.

[11] Patent Number: 5,425,700
[45] Date of Patent: Jun. 20, 1995

[54] GRAVITY OPERATED ORTHOTIC BRACE DROP LOCK

[75] Inventors: Gordon V. Aaserude, El Sobrante; James D. Mercer, Alamo, both of Calif.

[73] Assignee: Omni Scientific, Concord, Calif.

[21] Appl. No.: 198,991

[22] Filed: Feb. 18, 1994

[51] Int. Cl.⁶ .............................................. A61F 5/00
[52] U.S. Cl. .................................... 692/16; 602/26
[58] Field of Search .................... 602/5, 16, 23, 26; 16/231, 319, 324, 357; 623/27, 39–41, 43, 44

[56] References Cited

U.S. PATENT DOCUMENTS

| | | | |
|---|---|---|---|
| 2,433,570 | 12/1947 | Markkula | 602/26 X |
| 2,433,571 | 12/1947 | Markkula | 602/26 X |
| 2,591,373 | 4/1952 | Petruch | 602/26 |
| 2,594,227 | 4/1952 | Smith | 602/26 X |
| 2,646,793 | 7/1953 | Swiech et al. | 602/16 |
| 4,672,955 | 6/1987 | Cooper | 602/16 X |
| 4,915,098 | 4/1990 | Young et al. | 602/16 |
| 4,928,676 | 5/1990 | Pansiera | 602/16 |
| 5,108,455 | 4/1992 | Telikicherla | 623/33 |

OTHER PUBLICATIONS

*Prosthetics and Orthotics Catalogue*, distributed by Keiai Orthopedic Appliance Co., Ltd., Tokyo, Japan, front cover, pp. 43–44, 61–62, 65, 69 and back cover.

Primary Examiner—Linda C. M. Dvorak
Attorney, Agent, or Firm—John Bucher; Harry A. Pacini

[57] ABSTRACT

A gravity operated locking device and method of operation are disclosed for use with an orthotic brace of a type having upper and lower members hinged together for articulation of the brace with flexion and extension of a limb joint, the locking device comprising a housing adapted for ready attachment to or ready detachment from a portion of the brace, preferably the upper brace member, and forming a groove extending along the length of the housing for receiving a drop bolt tapered at its lower end for riding over and locking into engagement with a projecting stop surface on the lower brace member. The drop bolt is preferably formed with an elongated slot captured by a portion of an attachment means for the brace. The locking device may include an overriding lock for securing the brace in either a fixed, fully extended condition or free for articulation. With the overriding lock released, the drop bolt may be manually operated for selectively permitting either articulated or locked operation of the brace.

10 Claims, 2 Drawing Sheets

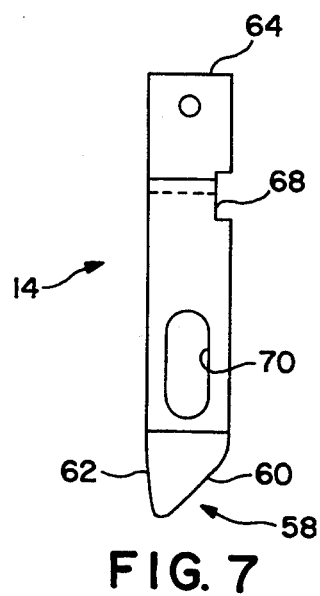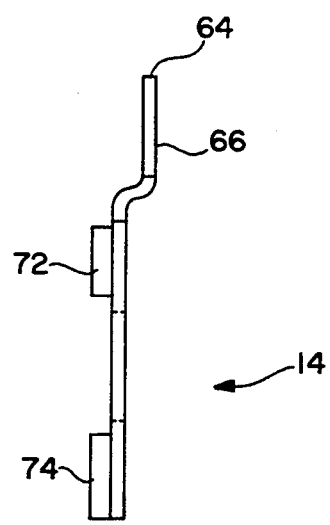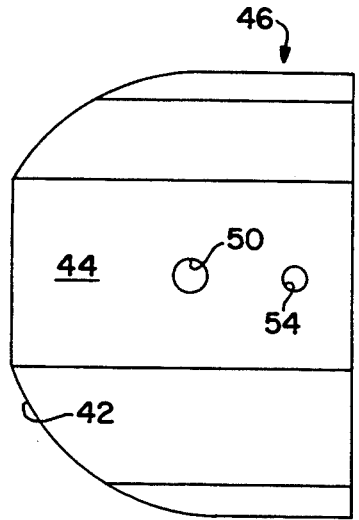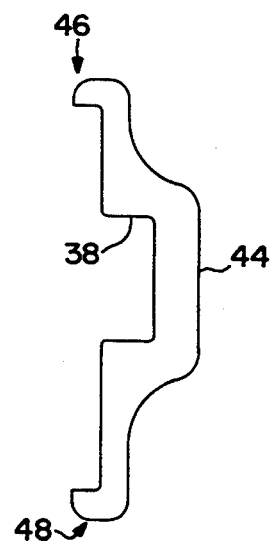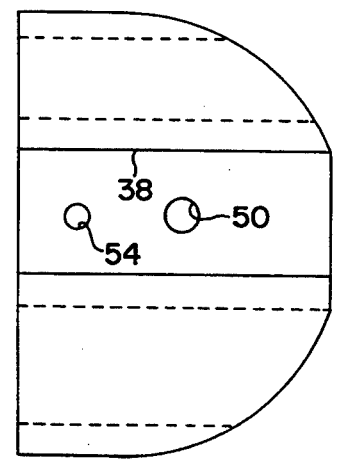

GRAVITY OPERATED ORTHOTIC BRACE DROP LOCK

FIELD OF THE INVENTION

The present invention relates to a locking device for use with orthotic braces and, more particularly, to a gravity operated locking device for use on an orthotic brace to lock the brace in full extension when in a vertical position.

BACKGROUND OF THE INVENTION

Orthotic braces are generally used for the support and bracing of weak or ineffective muscles or joints, especially for the support of knees or other joints of the limbs. An orthotic knee brace is generally an orthotic leg brace having an upper section which is removably attached to the upper leg and a lower section removably attached to the lower leg. The two sections may be hinged together at their intersection near the knee to allow for articulation with the knee movement while providing support for the knee.

Orthotic braces may be employed in long-term orthopedic devices for patients in the correction of permanently weakened or ineffective leg muscles, bones or knee joints. In this regard, a brace such as a knee brace would generally be lockable into a rigid and fully extended position where the upper and lower sections are roughly parallel to each other and to the axis of the extended limb. This arrangement allows for the support of the knee joint when it is in a completely extended and full weight-beating position such as when the brace user is standing or walking. Such braces may also be releasable from their fully extended position to articulate with the flexion of the joint such as when the user is sitting. Orthotic braces of this type may also be employed for use with lower extremity prosthetics.

Similar orthotic braces may be employed in rehabilitation devices for patients recovering from leg trauma such as broken bones, ligament damage, muscle damage, knee joint damage, sports injury, related surgery injury and the like. In this regard, the brace may be fixed in a rigid, fully extended position as above to immobilize the leg or knee joint and provide rigid support for the leg or knee, without being releasable to allow articulation of the knee joint. Such orthotic brace rehabilitation devices may be replaced with braces such as those used for long-term orthopedics which allow for articulation with the limb movement during the course of patient rehabilitation.

Orthotic braces of the type referred to immediately above are disclosed, for example, in the Prosthetics and Orthotics Catalogue distributed by Keiai Orthopedic Appliance Co., Ltd. This reference provides representatives of a variety of lower limb orthotic braces currently available.

Keiai knee braces generally comprise above-knee and below-knee bars respectively attachable to the upper and lower leg of the user and which are pivotally attached to each other at a hinged joint aligned near the user's knee joint. These braces are movable about the hinge joint from an extended position corresponding to a fully vertical or straightened leg, to an articulated position corresponding to the flexion of a bent leg. The Keiai braces are further constructed so that cooperation of the upper and lower bar members only allows for articulation between the fully extended position and movement in one direction, corresponding to the normal articulation of a leg. In this regard, the braces prevent over-center operation, or in other words, prevent the knee joint from traveling past its fully extended position.

Orthotic braces such as knee braces available under the Keiai trade name are generally attached to a patient's leg by use of thigh and calf bands. These bands may be made up of a variety of materials such as leather, plastics, metals or curable composite materials and are generally permanently fixed to the brace members after those brace members have been bent into S-shapes to conform with the contours of the patient's leg. The brace members may also be attached to a patient's leg by being integrated into a cast or other rehabilitative device.

Keiai knee braces are available in a variety of models ranging from those which are free hinging between fully extended and articulated positions, to those including locking devices which act to lock the brace in the fully extended position. Typical locking mechanisms include ring-slide locks, french locks, drop locks and drop locks with stoppers.

Drop locks as disclosed by the Keiai reference, such as the parts numbered K-109 and K-110, generally comprise a slidable collar arranged on the upper bar member of the brace. When the brace is in an articulated position, the collar is moved on the upper bar member to a non-locking position on that member generally well above the hinge joint of the brace. When the brace user is in a vertical or standing position, the collar travels down the brace member under the influence of gravity to a locked position where the collar engages a cam surface on the lower member arranged above the hinge joint. In the locked position the collar rests just above the hinge joint of the brace and prevents the lower member from moving in relation to the upper member.

Once a Keiai brace with a slidable collar drop lock mechanism is integrated into an assembled orthotic device, that locking mechanism is generally not removable or detachable without the subsequent removal and disassembly of the orthotic brace device. In this regard, a brace user no longer desirous of the locking feature provided by the collar mechanism must incur the time and cost of obtaining a new brace device assembled without the inclusion of the locking mechanism. Further, such locking devices are not attachable to an assembled orthotic brace device, such as where a brace user desires the addition of the locking feature to an existing brace. Here, as above, the brace user must incur the added time and expense of obtaining a new orthotic device having a locking mechanism in place.

French locks as disclosed by Keiai, such as the pans numbered K-103 and K-104, generally comprise a lever attached to the upper member of a brace which cooperates with a notched surface on the lower brace member. Here, the notched surface is arranged above the hinge joint and engages the lever in a locked position above the hinge joint when the brace is in its fully extended position. The lever is then releasable out of its locking engagement with the notched surface, allowing the brace to articulate with the flexion of the knee joint.

As with the slidable collar drop lock mechanisms above, the french lock mechanism is generally permanently fixed to an assembled orthotic brace device. In this regard, the french lock mechanism is likewise not readily attachable or detachable on an existing device. A brace user desirous of either obtaining or removing the locking feature provided by the french lock will need to incur the time and expense of having a new orthotic brace assembled with or without the french lock in place.

Ring-slide locks under Keiai, such as the parts numbered K-101 and K-102, are generally improved drop locks where the collar has further means for urging the collar into its locked position. Here, a lock bar is attached to the collar and fixed to the upper brace member by a guide means. A compression spring is arranged between the collar and the lock guide means on the lock bar to urge the collar into its locked position above the brace hinge joint. The lock is releasable by pulling the lock bar upwards, against the spring direction, to slide the collar out of engagement with the lower brace member cam surface.

The additional hardware associated with the lock bar, guide means and compression spring means causes these locking mechanisms to be generally permanently fixed to an assembled orthotic brace device. As above, the lack of removability and attachability of these locking devices to existing braces leads to added time and expense for users wishing to remove or add the french lock device to an existing brace.

Orthotic braces of the type referred to above are further disclosed by the Catalogue of OMNI Scientific, Inc. One such knee brace, available under the Trade name of the OMNI brace, comprises generally the same parts as those disclosed by Keiai with the added feature of an adjustable fixed extension setting for selecting the angular relation of the upper and lower brace members when they are in the fully extended position.

In this regard, the OMNI brace comprises an upper brace member or bar which is pivotally attached to a shackle at its lower terminus where the shackle is arranged generally near the knee joint. The shackle is further adjustably fixed to the upper brace bar in a position such as 0, 10, 20 or 30 degrees relative to the axis of the upper brace bar, thereby preventing the upper brace member from pivoting in relation to the shackle. The OMNI brace shackle is then pivotally attached at its other end to the upper terminus of the lower brace member or bar. In this manner, the fully extended position of the brace is fixed with the axes of the upper and lower brace bars at 180, 170, 160 or 150 degrees relative one another.

With the inclusion of a shackle at the hinged joint of a knee brace, such as in the OMNI brace, prior an locking mechanisms such as those employing slidable collars are inadequate to provide a simple and effective means to lock those braces into a fully extended position. Further, prior art locking devices such as drop rings, slidable collars or french locks are generally not removable from or attachable to an assembled orthotic brace in situ, especially after the brace has been attached to a patient's limb. Accordingly, there has been found to remain a need for further improvements in locking devices for orthotic braces.

SUMMARY OF THE INVENTION

The present invention is drawn toward the provision of a flexion lock release and gravity-operated locking system for use with orthotic braces where the locking system is capable of allowing instantaneous flexion motion or immediate resumption to a fixed, fully extended position in the orthotic brace. In this regard, it is an object of the present invention to provide a self locking device for use on orthotic braces, such as a knee brace, to lock the brace in full extension when it is in a vertical position where the locking device is easily unlocked to allow flexion of the brace when desired.

It is a more particular object of the invention to provide a gravity-operated locking device for use with orthotic braces of the type having upper and lower bar members respectively attached to upper and lower portions of a patient's limb and parallel to the axis of the limb, the bar members being hinged together at or near the limb joint to articulate with the extension and flexion of the limb, where the locking device comprises a housing secured to the upper bar member of the brace, the housing having a groove extending generally parallel to the axis of the upper brace bar member, and a drop bolt being slidable within the housing groove between an extended (locked) position and a retracted (unlocked) position where the lower end of the drop bolt —when extended— engages a projection on the lower brace bar member to lock the brace into a fully extended position. In this manner, the drop bolt of the locking device moves into its locked position under the influence of gravity as the brace is articulated to its fully extended vertical position, and is manually retractable to release the brace and allow flexion of the brace and, accordingly, the corresponding limb.

It is a more specific object of the present invention to provide the gravity-operated locking device described immediately above for use on orthotic braces of the type available under the OMNI brace trade name.

It is an even more particular object of the present invention to provide a gravity-operated locking device which is readily attachable in situ to, and likewise detachable in situ from an assembled orthotic brace, even after the brace has been attached to a patient's limb in either an orthopedic or rehabilitative device. In this regard, attachment means for the locking device comprising for example a common screw which cooperates with an existing threaded element on an assembled brace allows for easy attachment or removal of the locking device by the user or an attending orthopedic care supplier. The addition of the gravity-operated locking device of the present invention to a brace such as an OMNI brace readily converts it into a post-operative or post-injury rehabilitation device. Upon simple removal of the locking device, the brace is converted back to an orthotic brace having relatively unrestricted flexion motion.

It is a related object of the present invention to provide a gravity-operated locking device for use with orthotic braces where the locking device further comprises means to secure the lock in either an extended (locked) position or in a retracted (unlocked) position. In this manner, the locking device may be secured in its locked position to fix the orthotic brace in a fully extended position. The locking device may alternatively be secured in its retracted position to allow full flexion of the orthotic brace.

Additional objects and advantages of the invention are described below with reference to the accompanying drawings.

BRIEF DESCRIPTION OF THE DRAWINGS

FIG. 6 is a side view of a drop bolt forming part of the locking device.

FIG. 7 is a plan view of the drop bolt.

FIG. 8 is a top view of a housing for the locking device.

FIG. 9 is an end view of the housing of FIG. 8.

FIG. 10 is a bottom view of the housing of FIG. 8.

DESCRIPTION OF THE PREFERRED EMBODIMENTS

Figure 1:
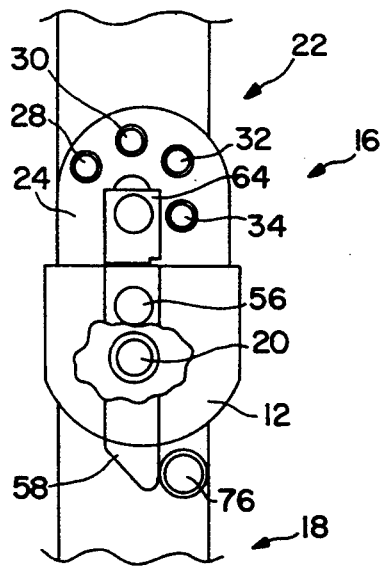
FIG. 1 is a plan view of the gravity operated locking device in combination with an orthotic brace.
Figure 2:
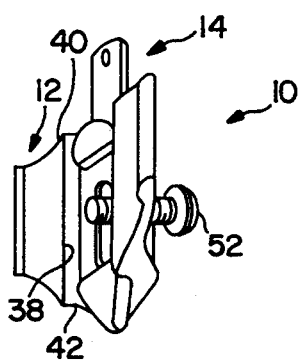
FIG. 2 is a pictorial view of the components of the gravity operated locking device.
Figure 3:
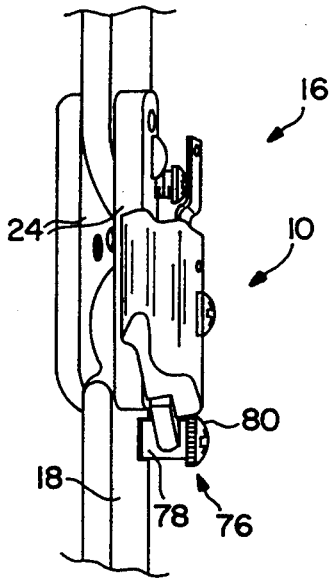
FIG. 3 is a pictorial representation of the locking device mounted upon the orthotic brace.

Referring now to the drawings and particularly to FIGS. 1-3, a gravity operated locking device constructed in accordance with the present invention is generally indicated at 10 and comprises a housing 12 and drop bolt 14 described in greater detail below.

Figure 4:
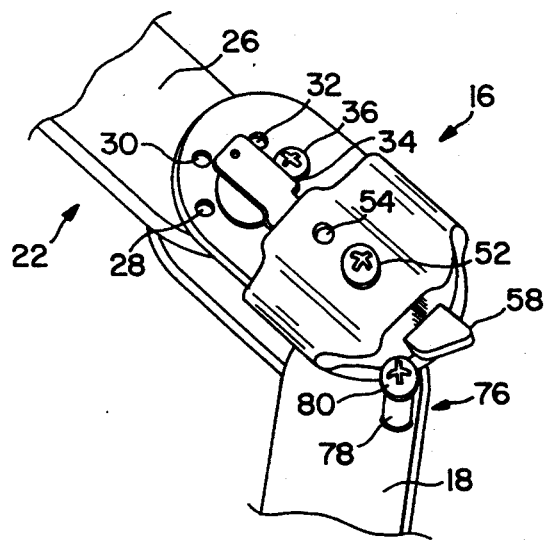
FIG. 4 is a view similar to FIG. 3 with the locking device unlocked and the brace in a flexed position.
Figure 5:
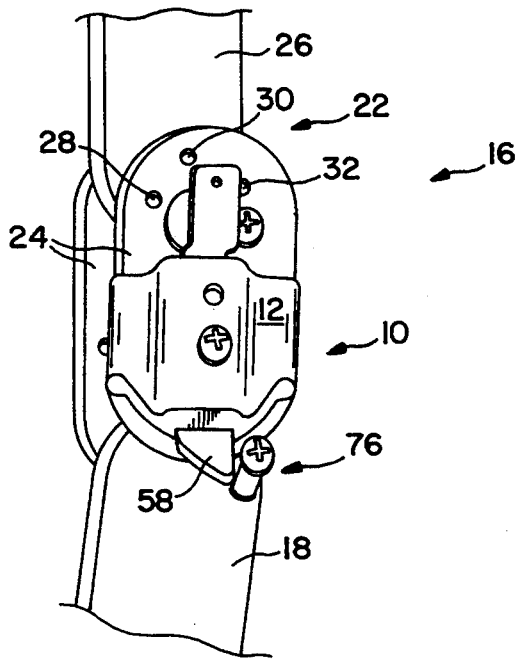
FIG. 5 is a similar view with the brace in a fully extended position and the locking device in a locked position.

The gravity operated locking device 10 is adapted for operation with and is accordingly illustrated in FIG. 1 as being attached to an orthotic brace 16. The orthotic brace 16 is also illustrated in FIGS. 3-5 together with the locking device 10 and comprises a lower member 18 interconnected by means of a hinge pin 20 to an upper member 22. The hinge pin 20 may preferably include a threaded seat therein (not shown) for readily receiving attachment of the locking device 10 as discussed in greater detail below.

The orthotic brace 16 is of a type well known in the prior art for use as an orthopedic device as described in greater detail above. Generally, the orthotic brace 16 is adapted for attachment to a limb so that the lower member 18 moves with a lower portion of the limb, for example the lower leg, while the upper member 22 remains fixed to an upper portion of the limb, for example, the upper leg. In this arrangement, the hinge pin 20 of course generally corresponds with the knee. Orthotic braces of this general type are well known as indicated above. More preferably, the orthotic brace 16 is of a type available for example from Omni Scientific, Inc. and referred to as the OMNI brace. In the OMNI brace, the upper member 22 is preferably formed by a first portion or hinge plates 24 interconnected with the lower member 18 by means of the hinge pin 20. The upper member 22 also includes a second portion or bar 26 forming an extended portion of the orthotic brace. The first and second portions of the upper member are preferably adapted for angular adjustment by means of a plurality of holes 28-34 formed for example in the first portion 24. A screw 36 may be arranged in any of the holes, for example the hole 34 as illustrated in FIG. 4 and secured to the second portion 26 of the upper member.

As noted above, the brace 16 is illustrated in a fully extended position in FIG. 5. In FIG. 4, the lower member 18 is pivoted or flexed in one direction from the fully extended position of FIG. 5. The orthotic brace 16 also includes means (not shown) for preventing overcenter operation of the brace in a pivoted or flexed direction opposite that illustrated in FIG. 4.

To describe the locking device 10 in greater detail, the housing 12 is of a generally flat configuration selected for mounting on a portion of the orthotic brace 16 as described in greater detail below. The housing 12 is formed with an elongated groove 38 extending along the entire length of the housing 12 between its upper and lower ends 40 and 42. As best illustrated in FIGS. 8-10, the housing 12 is preferably formed with an elongated, raised portion 44 containing the elongated groove 38. The housing 12 additionally has side rails 46 and 48 extending along its length for encompassing a portion of the orthotic brace 16 as also described in greater detail below.

The housing 12 is preferably adapted for attachment to the upper member 22 of the orthotic brace 16 and more particularly to the first portion or hinge plates 24. For that reason, the side rails 46 and 48 are spaced apart from each other in order to encompass part of the shackle 24. The housing 12 is also formed with an opening 50 for receiving an attachment means which serves to attach the housing 12 to the shackle 24. Preferably, the attachment means comprises a screw 52 engaging a threaded seat (not shown) in the hinge pin 20, the screw 52 extending through the groove 38 and the drop bolt 14. The housing 12 also forms an additional opening 54 for receiving an overriding locking device 56 described in greater detail below.

The drop bolt 14 is an elongated flat pin as illustrated in FIGS. 6 and 7. A lower end 58 of the drop bolt 14 is formed with a tapered surface 60 generally facing in the direction of pivotal movement or flexure for the lower brace member 18. The lower end 58 of the drop bolt 14 also has an oppositely tapered stock surface 62 for engaging the projecting stop surface on the lower brace member 18.

An upper end 64 of the drop bolt 14 is formed with a projecting portion 66 to facilitate manual operation of the drop bolt 14 as described below. The upper end of the drop bolt 14 could also be provided with a knob (not shown) or the like to further facilitate manual operation thereof. A notch 68 may be formed on one side of the upper end of the drop bolt merely for the purpose of clearing the screw 36 when it is in the hole 34 as illustrated in FIG. 4, for example. A recessed screw at 36 will avoid the necessity of notch 68.

The drop bolt 14 also forms an elongated slot 70 for receiving the attachment means as described above. The length of the elongated slot 70 is selected to generally limit travel of the drop bolt between an extended position illustrated for example in FIG. 1 and in retracted position where the drop bolt is raised as described above.

The housing 12 and drop bolt 14 are assembled together as generally illustrated in FIG. 2 and mounted on the hinge plates 24 of the brace as illustrated for example in FIGS. 1 and 3. The locking device is readily mounted upon the brace simply by attaching the threaded screw 52 to the threaded seat in the hinge pin 20.

With the locking device 10 attached to the brace by means of the screw 52, the drop bolt 14 is captured by the screw 52 passing through the elongated slot 70. Referring again to FIGS. 6 and 7, the drop bolt 14 also may include spacer weight blocks 72 and 74 mounted on a lower surface of the drop bolt 14 generally adjacent opposite ends of the elongated slot 70. The spacer blocks may be avoided by fabricating the drop bolt 14 of thick one piece stock of mass equivalent to the drop bolt with spacer weight blocks.

The overriding locking device 56, preferably a screw including a knurled knob, is then arranged in the opening 54 for engagement with the drop bolt 14.

An additional portion of the locking device 10 comprises a projecting stop surface 76 arranged on the lower member 18 for stopping engagement with the lower end 58 of the drop bolt 14. Preferably, the projecting stop surface 76 is formed by a cylindrical post 78 secured to the lower member by means of a screw 80.

Accordingly, there has been described above a gravity operated locking device 10 which may be readily attached to and operated in combination with an orthotic brace such as that indicated at 16. The locking device 10 may readily be detached from an assembled brace as discussed above. The operation of the locking device 10 in combination with the brace 16 is believed to be apparent from the preceding description. However, its operation is briefly described below in order to assure a more complete understanding of the invention.

In operation, the components of the locking device including the housing 12 and drop bolt 14 are assembled as illustrated in FIG. 2 and then attached to the brace 16, for example, by means of the screw 52 as illustrated in FIGS. 3 and 4. The locking device 10 may be readily attached to the brace 16 before or after assembly of the brace into an orthotic brace device. With the drop bolt 14 being arranged within the groove 38, it is captured by the screw 52 passing through the elongated slot 70.

With the locking device 10 attached to the orthotic brace, it may be employed for either fully articulated movement of the brace or for operation of the brace in a locked, fully extended position. Initially, the drop bolt 14 may be locked in either a fully extended position where its tapered lower end 62 engages the projecting stop surface 76 as illustrated in FIG. 5 or in a fully retracted position for preventing engagement of the drop bolt 14 with the stop surface 76.

In addition, the brace 16 may be employed for permitting selective articulated movement at the option of the wearer. For this purpose, the overriding locking device 56 is released so that the drop bolt 14 can move within the groove 38 of the housing. In this condition, when the upper and lower members of the brace approach a fully extended vertical position as illustrated in FIG. 5, the drop bolt is urged down under the influence of gravity so that the tapered surface 60 rides over the projecting stop surface 76 and the stop surface 76 then engages the tapered stop surface 62 for securing the brace in the fully extended condition.

Optionally, the drop bolt 14 may be raised or retracted by the projecting portion 66 to selectively permit articulation of the brace with the lower member 22 pivoting in the direction illustrated in FIG. 4. If the user then releases the drop bolt 14, it returns to its fully extended position so that it will again ride over and engage the stop surface 76 when the brace is articulated to its fully extended position.

Further, once the user no longer desires the self locking function provided by the locking device 10, the user can readily detach the locking device from the brace 16 to convert the orthotic brace to one having relatively unrestricted flexion motion.

Accordingly, there has been described above both a novel gravity operated locking device and its method of operation in combination with an orthotic brace. Additional modifications and variations, in addition to those described above, are believed to be apparent. Accordingly, the scope of the invention is defined only by the following appended claims which are further exemplary of the invention.

What is claimed is:

1. A gravity-operated locking device for use with an orthotic brace having an upper member pivotally connected to a lower member by a hinge for articulation of the brace with flexion and extension of a limb joint, the gravity-operated locking device comprising:

a housing having upper and lower ends wherein the housing is adapted to be secured to the upper member of the orthotic brace, the housing forming a groove extending from the upper end to the lower end of the housing and for arrangement generally parallel to the axis of the upper member of the brace:

a drop bolt having upper and lower ends, the drop bolt being movable within the housing groove between an extended position where the lower end of the drop bolt is adapted for protecting beneath the lower end of the housing for locking engagement with a surface portion on the lower brace member and a retracted position where the lower end of the drop bolt is adapted for being out of engagement with the surface portion on the lower brace member to permit the brace members to articulate with flexion and extension of the limb joint; and attachment means for readily attaching and detaching the housing relative to the upper member of the orthotic brace, the attachment means passing through the housing groove and adapted to be secured to the upper member of the brace, the attachment means further passing through a slot in the drop bolt whereby the length of the slot is adapted to limit relative travel of the drop bolt and the attachment means is readily attachable to and detachable from an assembled orthotic brace.

2. The gravity-operated locking device of claim 1 wherein the removable attachment means for securing the locking device housing to the upper member of the orthotic brace comprises a screw adapted for threadably communicating with a complementary threaded seat on the upper member of the brace.

3. The gravity-operated locking device of claim 1 further comprising means for securing the locking device with its drop bolt in either its extended position or in its retracted position for causing the orthotic brace to operate either as a rigid and fully extended unit or as a fully articulable unit.

4. The gravity-operated locking device of claim 1 in combination with the orthotic brace wherein the drop bolt has a tapered surface with an opposing locking surface on its lower end and further comprising a projection which the drop bolt engages on the lower brace member, the projection comprising a stop means for the locking device.

5. The gravity operated locking device and orthotic brace of claim 4 wherein the stop means extends out from the lower brace member and past the travel of the extended drop bolt, the drop bolt having its tapered surface arranged so that it will ride over the stop means as the orthotic brace is articulated toward its fully extended position to allow the drop bolt to fall behind the stop means with its locking surface in engagement with the stop means to prevent articulation of the brace in the opposite direction.

6. The gravity-operated locking device and orthotic brace of claim 5 wherein the stop means comprises a cylindrical post attached to the lower brace member and wherein the locking surface on the lower end of the drop bolt has a slight taper to assure full contact of the drop bolt locking surface with the cylindrical stop means.

7. The gravity-operated locking device of claim 1 for use with an orthotic brace having an upper member pivotally connected to a lower member by a hinge for articulation of the brace with the flexion and extension of the limb joint, the brace further having locking means for limiting articulated movement between the upper and lower members of the brace to prevent articulated operation of the brace beyond its fully extended position, wherein the locking function of the gravity-operated locking device operates in opposition to the locking function of the brace locking means to render the brace completely rigid.

8. The gravity-operated locking device of claim 1 for use with an orthotic brace having an upper member comprising a first element pivotally connected to a lower member by a hinge and a second element adjustably attached to the first element for selecting the angle of the second element of the upper member in relation to the lower member when the brace is in the fully extended position, wherein the gravity-operated locking device housing is adapted for being secured to the first element portion of the upper member of the brace with the housing arranged generally parallel to the axis of the first element portion.

9. The gravity-operated locking device of claim 8 in combination with the orthotic brace wherein the locking device housing is arranged so that the lower end of the housing extends downwardly past the hinge connecting the first upper member element with the lower member of the orthotic brace, the lower end of the fully extended drop bolt projecting downwardly past the hinge for engagement with a surface portion on the lower member of the brace also arranged below the hinge.

10. The gravity-operated locking device of claim 1 in combination with the orthotic brace wherein the gravity-operated locking device housing is arranged so that the lower end of the housing extends downwardly past the hinge connecting the upper and lower members of the orthotic brace, the lower end of the fully extended drop bolt projecting downwardly past the hinge for engagement with a surface portion on the lower member of the brace also arranged below the hinge.

* * * * *